(12) United States Patent
Becker et al.

(10) Patent No.: US 8,319,633 B2
(45) Date of Patent: Nov. 27, 2012

(54) LOCATION DETECTION SYSTEM FOR A PATIENT HANDLING DEVICE

(76) Inventors: David Terrance Becker, Grand Rapids, MI (US); Bruce L. MacDonald, Portage, MI (US); Joseph E. Mroz, Hastings, MI (US); Michael Joseph Hayes, Kalamazoo, MI (US); Christopher John Hopper, Kalamazoo, MI (US); Richard C. Mayoras, Jr., Kalamazoo, MI (US); Martin W. Stryker, Kalamazoo, MI (US); Vivek Shankar, Kalamazoo, MI (US); Jean-Paul Dionne, Lévis (CA); Aaron Douglas Furman, Kalamazoo, MI (US); Krishna Sandeep Bhimavarapu, Portage, MI (US)

( * ) Notice: Subject to any disclaimer, the term of this patent is extended or adjusted under 35 U.S.C. 154(b) by 0 days.

(21) Appl. No.: 13/356,204

(22) Filed: Jan. 23, 2012

(65) Prior Publication Data
US 2012/0176221 A1    Jul. 12, 2012

Related U.S. Application Data

(63) Continuation of application No. 12/573,545, filed on Oct. 5, 2009, now Pat. No. 8,102,254, which is a continuation of application No. 11/277,838, filed on Mar. 29, 2006, now Pat. No. 7,598,853.

(60) Provisional application No. 60/665,955, filed on Mar. 29, 2005, provisional application No. 60/734,083, filed on Nov. 7, 2005.

(51) Int. Cl.
*G08B 1/00*    (2006.01)

(52) U.S. Cl. ............ 340/539.12; 340/539.1; 340/539.11

(58) Field of Classification Search ............... 340/539.1, 340/539.11, 539.12
See application file for complete search history.

(56) References Cited

U.S. PATENT DOCUMENTS

| 4,363,137 | A | 12/1982 | Salisbury |
| 4,677,599 | A | 6/1987 | Obayashi et al. |
| 4,688,026 | A | 8/1987 | Scribner et al. |
| 4,958,645 | A | 9/1990 | Cadell et al. |
| 5,062,151 | A | 10/1991 | Shipley |

(Continued)

FOREIGN PATENT DOCUMENTS

EP    1623666    12/2009

(Continued)

OTHER PUBLICATIONS

International Application No. PCT/US2006/011600, International Search Report filing date Mar. 29, 2006 and Written Opinion, Applicant's file No. 60,252-067.

*Primary Examiner* — Travis Hunnings
(74) *Attorney, Agent, or Firm* — Warner Norcross & Judd LLP

(57) ABSTRACT

A location detection system for a facility includes a patient handling device with a communication module with a unique ID, a locator fixed relative to the handling device for transmitting a unique location identifier corresponding to the location of the handling device, and a receiver mounted to the patient device for receiving the unique location identifier. A processing station remote from the handling device and the locator receives the unique location identifier and the unique ID and further correlates the unique ID with a patient supported by the handling device wherein the processing station can track the handling device and the patient supported thereby such that the location of the patient and handling device can be determined and monitored remotely from the handling device.

20 Claims, 12 Drawing Sheets

U.S. PATENT DOCUMENTS

| | | | |
|---|---|---|---|
| 5,699,038 A * | 12/1997 | Ulrich et al. | 340/286.07 |
| 5,708,421 A | 1/1998 | Boyd | |
| 5,742,238 A | 4/1998 | Fox | |
| 5,764,162 A | 6/1998 | Ehrlich | |
| 5,963,133 A | 10/1999 | Monjo | |
| 6,078,261 A * | 6/2000 | Davsko | 340/573.4 |
| 6,293,699 B1 | 9/2001 | Bailey et al. | |
| 6,593,845 B1 | 7/2003 | Friedman et al. | |
| 6,885,288 B2 | 4/2005 | Pincus | |
| 6,970,097 B2 | 11/2005 | Welles, II et al. | |
| 7,034,690 B2 | 4/2006 | Chaco | |
| 7,099,895 B2 | 8/2006 | Dempsey | |
| 7,598,853 B2 * | 10/2009 | Becker et al. | 340/539.13 |
| 8,102,254 B2 * | 1/2012 | Becker et al. | 340/539.12 |
| 2001/0033267 A1 | 10/2001 | Kim et al. | |
| 2002/0014951 A1 * | 2/2002 | Kramer et al. | 340/5.8 |
| 2004/0051860 A1 | 3/2004 | Honda et al. | |
| 2004/0106854 A1 * | 6/2004 | Muraki | 600/300 |
| 2004/0111024 A1 * | 6/2004 | Zheng et al. | 600/426 |
| 2004/0161246 A1 | 8/2004 | Matsushita et al. | |
| 2005/0093709 A1 | 5/2005 | Franco, Jr. et al. | |
| 2005/0122119 A1 | 6/2005 | Barlow | |
| 2005/0151640 A1 | 7/2005 | Hastings | |
| 2006/0092072 A1 | 5/2006 | Steiner | |
| 2006/0135083 A1 | 6/2006 | Leinonen et al. | |

FOREIGN PATENT DOCUMENTS

| | | |
|---|---|---|
| WO | 9718639 | 5/1997 |
| WO | 03105095 | 5/2003 |
| WO | 2004093023 | 4/2004 |
| WO | WO 2004/104619 | 12/2004 |

* cited by examiner

LOCATION DETECTION SYSTEM FOR A PATIENT HANDLING DEVICE

CROSS REFERENCE TO RELATED APPLICATION

This application is a continuation application of U.S. patent application Ser. No. 12/573,545, filed Oct. 5, 2009, by David T. Becker, et al., entitled LOCATION DETECTION SYSTEM FOR A PATIENT HANDLING DEVICE, which will issue on Jan. 24, 2012 as U.S. Pat. No. 8,102,254, which is a continuation of U.S. Pat. No. 7,598,853, issued Oct. 6, 2009, which claims the benefit of U.S. provisional patent application Ser. No. 60/665,955, filed Mar. 29, 2005 and U.S. provisional patent application Ser. No. 60/734,083, filed Nov. 7, 2005, which are incorporated by reference herein in their entireties.

FIELD OF THE INVENTION

The present invention generally relates to location detection systems for use in facilities such as healthcare facilities for tracking equipment such as patient handling devices. More specifically, the present invention relates to the location detection system having locators programmed with unique location identifiers to determine a location of the patient handling devices.

BACKGROUND OF THE INVENTION

Location detection systems are well known in the art for tracking the location of personnel and equipment in a facility. These systems have been specifically adapted for use in facilities such as healthcare facilities for tracking healthcare professionals, e.g., nurses and physicians, and for tracking equipment, e.g., beds, patient monitoring devices, and the like. A typical location detection system is also referred to as an asset tracking system that utilizes tags that periodically transmit a unique identification signal. Receivers are located throughout the facility at known locations for receiving these identification signals. The receivers are wired to a central computer that processes the unique identification signals to determine a location of the asset associated with the tag.

One disadvantage of such systems is that a typical asset tracking system does not utilize existing infrastructure within the healthcare facility. As a result, the capital costs necessary to provide the infrastructure to accommodate asset tracking is high. For instance, the receivers used to receive the identification signals from the tags attached to the assets being tracked must be installed throughout the healthcare facility, as well as wired to the central computer. This requires considerable labor and expense, as well as lengthy disruptions to install the wiring.

In today's healthcare facilities, networks are provided for accessing patient data, equipment data, lab results, and the like. However, with current asset tracking systems, integrating information regarding the location of mobile equipment such as patient handling devices with patient data or other data available on the network is not practical. One reason that most asset tracking systems cannot be integrated wholly with current healthcare facility networks is that these asset tracking systems are only designed to identify a particular room in which a patient handling device is located. These systems are not designed to determine a specific zone in the room in which the patient handling device is located. In some healthcare facilities each room may accommodate two, three, or more patient handling devices. Therefore, when current asset tracking systems are used, the room location of each of the patient handling devices can be determined, e.g., the patient handling devices are in room 1, but they are not sensitive enough to determine that patient handling device no. 1 is in zone 1 of room 1, patient handling device no. 2 is in zone 2 of room 1, etc. In order for current asset tracking systems to provide this level of location detail, separate receivers are needed in each zone, with each receiver being wired to the central computer. As a result, the infrastructure costs further escalate.

Therefore, there is a need in the art for a location detection system that can easily be implemented in existing healthcare facilities with little capital investment and additional infrastructure while also providing specific location details that enable the location information to be fully integrated with other data such as patient data and other equipment data available on existing networks in the healthcare facility.

SUMMARY OF THE INVENTION AND ADVANTAGES

The present invention provides a location detection system for locating patient handling devices in a facility. A locator is fixed at a location relative to the patient handling device. The locator transmits a unique location identifier corresponding to the location of the patient handling device. A processing station, remote from the patient handling device and the locator, receives the unique location identifier such that the location of the patient handling device can be determined and monitored remotely from the patient handling device. A receiver is supported by the patient handling device for receiving the unique location identifier from the locator. A communication module is also supported by the patient handling device and is electronically coupled to the receiver for transmitting the unique location identifier from the patient handling device to the processing station. As a result, the patient handling device acts as a communication link between the locator and the processing station.

A method of detecting the location of the patient handling device is also provided. The method includes transporting the patient handling device to the location in the facility and transmitting the unique location identifier from the locator to the receiver of the patient handling device. The method also includes transmitting the unique location identifier from the patient handling device to the processing station remote from the patient handling device such that the location of the patient handling device can be determined and monitored remotely from the patient handling device.

This system and method have several advantages over the prior art. For instance, by placing the receiver on the patient handling device, the patient handling device acts as the communication link between the locator and the processing station. Furthermore, by transmitting the unique location identifier from the locator to the receiver and then on to the processing station, there is no need for additional infrastructure in the facility to support the locators. Locations can be determined simply by placing the locator, programmed with the unique location identifier, in the location of interest, and transmitting that location to the patient handling device, which then sends the unique location identifier onto the processing station. In another aspect of the invention, the patient handing device also transmits its own unique ID thereby correlating the location of the patient handling device to its unique ID. This will enable healthcare facilities to better track patients by associating patients with their patient handling devices and further associating the patient handling devices with their location in the healthcare facility, down to the specific zone in the room in which the patients and the patient handling devices are located.

In another aspect of the present invention, the location detection system comprises a first locating device associated with the patient handling device for transmitting a first unique location identifier to the processing station and a second locating device associated with the patient handling device for transmitting a second unique location identifier to the processing station. In this system, the first unique location identifier corresponds to a first area of the location and the second unique location identifier corresponds to a second area of the location different than the first area. In one embodiment, the first unique location identifier identifies the room in which the patient handling device is located and the second unique location identifier identifies the zone in the room in which the patient handling device is positioned. Therefore, the first locating device provides a general vicinity of the patient handling device, while the second location device further defines the location of the patient handling device in the general vicinity.

In another aspect of the present invention, existing asset tracking systems can be utilized to determine general vicinity information for the patient handling devices such as the room in which they are located, and the patient handling devices can be further outfitted with the second locating device to refine the location information down to the specific zone in the room in which the patient handling device is located.

In yet another aspect of the present invention, a method of detecting the location of the patient handling device using the first and second locating devices is provided. The method includes transporting the patient handling device to the location in the facility and transmitting a first unique location identifier to the processing station. The method also includes determining the first area location of the patient handling device from the first unique location identifier and transmitting a second unique location identifier to the processing station wherein the first unique location identifier corresponds to the first area of the location and the second unique location identifier corresponds to the second area of the location.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Referring to the figures, wherein like numerals indicate like or corresponding parts throughout the several views, a location detection system for a facility is generally shown at 20. The location detection system 20 is described as being integrated into a patient handling device 22 of a healthcare facility such as a hospital. Patient handling devices 22 include devices such as beds, stretchers, cots, wheelchairs, and the like. It should be appreciated that the concepts provided by the present invention could also be applied to other devices located in a healthcare facility including, but not limited to infusion pumps, patient monitoring devices, patient therapy devices such as stand-alone therapy mattresses, and the like. It should also be appreciated that these principles could be applied to non-healthcare facilities. For purposes of description, reference is generally made to healthcare facilities.

Figure 1:
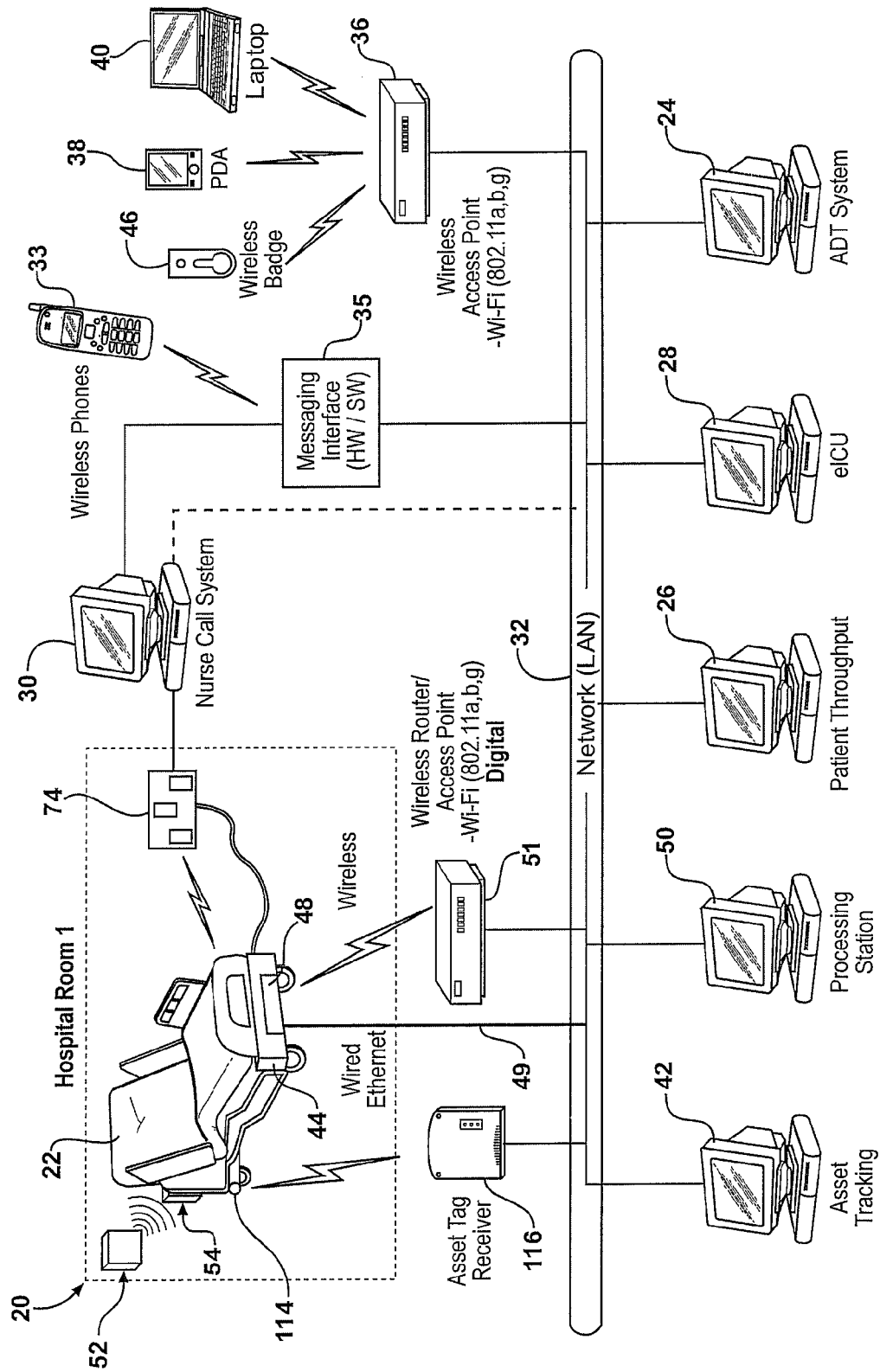
FIG. 1 is a schematic view of a healthcare facility with a network.

Referring to FIG. 1, the healthcare facility includes several systems that can be placed in electronic communication with one another through a common network 32. These systems include admission-discharge-transfer (ADT) systems 24 and patient throughput systems 26 such as those offered by Premise Development Corporation. These systems may also include eICU systems 28 such as those provided by Cerner Corporation for the remote monitoring of critically ill patients. A nurse call system 30 may also be in communication with the network 32. For instance, a nurse call system provided by Rauland-Borg Corporation can be used to instantly transfer nurse calls from a patient to the network 32, or to the patient's primary and/or secondary caregivers via a wireless phone 33 using well-known messaging interfaces 35. This places the patient in immediate contact with a healthcare professional to provide faster, more efficient service.

Several communication devices may also be used to access the data or information provided by these systems 24, 26, 28, 30 to receive messages or alerts from these systems 24, 26, 28, 30, or to transmit information to these systems 24, 26, 28, 30. For instance, a wireless badge 46 may be in communication with these systems 24, 26, 28, 30 via wireless access points 36 provided throughout the healthcare facility. Healthcare professionals, e.g., nurses, nurse's aides, medical assistants, nurse practitioners, physician assistants, physicians, etc., may carry the wireless badges 46 to alert the nurse when a patient has called for assistance, or that an alarm condition is present. The nurse could also use the wireless badge 46 to speak to a voice recognition system to report an alarm condition, or to report that the nurse has completed a task, to report any event that may occur in the healthcare facility. Personal digital assistants (PDAs) 38 could also be in communication with the networked systems 24, 26, 28, 30 to transfer data and information between the PDAs 38 and the network 32. Similarly, laptop computers 40 could be used to transfer data and information.

Asset tracking systems 42 may also be integrated into the network 32. Such systems 42 may include those offered by Radianse, Inc., Versus Technology, Inc. or others to track assets throughout the healthcare facility. In some embodiments, the location detection system 20 is intended to operate independently of the asset tracking system 42 to specifically identify the location, e.g., room and zone, of the patient handling devices 22. In other embodiments, the location detection system 20 of the present invention is intended to work in conjunction with the asset tracking system 42 to identify the location of the patient handling devices 22 in the healthcare facility.

Still referring to FIG. 1, in one embodiment of the present invention, the patient handling device 22 is adapted for communicating with the network 32. More specifically, a central processing unit 44 (CPU) of the patient handling device 22 is in electronic communication with the network 32 via a communication module 48. The CPU 44 carries out the functions of the patient handling device 22 such as motor functions for raising or lowering movable sections of the patient handling device 22 in response to user input, sensing functions for sensing siderail positions, bed height, patient position or bed exit, patient weight, brake positions, and the like, as will be appreciated by those skilled in the art, or therapy functions for a therapy mattress, such as rotation, percussion, or vibration functions. The CPU 44 includes the necessary processors and memory for carrying out these functions as will be appreciated by those skilled in the art.

The CPU 44 and communication module 48 are physically supported by the patient handling device 22 to move with the patient handling device 22 from location to location. Preferably, one or more housings enclose the CPU 44 and the communication module 48 with the housing or housings being mounted to a frame of the patient handling device 22. As a result, all of the hardware necessary for connecting the CPU 44 of the patient handling device 22 to the communication module 48 is located on and supported by the patient handling device 22. It should be appreciated that the CPU 44 and the communication module 48 could be integrated into a single chassis or could be separate connectable components linked together in a wired or wireless configuration. By providing the communication module 48 on the patient handling device 22, the patient handling device 22 acts as a communication center or link for transmitting data and/or information related to the patient handling device 22, including its location, to the network 32.

The communication module 48 may be connected to the network 32 via a wired and/or wireless connection to transfer data and/or information back and forth between the CPU 44 and the hospital network 32. In a wired configuration, the communication module 48 may be a transceiver wired through a communication link 49 to the hospital network 32. The communication link may be an RS-232 cable, and Ethernet-compliant cable, or any other wired connection known to those skilled in the art. In a wireless configuration, the communication module 48 may be a wireless transceiver or router that is configured with a compatible wireless transceiver or router 51 located on the hospital network 32. In some embodiments, both wired and wireless configurations are present on the patient handling device 22 to easily accommodate user preferences. It should be appreciated that in some patient handling devices 22, there is no CPU 44, but instead a plurality of electronic modules that communicate on a peer-to-peer network. In this instance, the communication module 48 is simply one of the modules or nodes in the peer-to-peer network. However, for purposes of description, reference is made to a master/slave system utilizing the CPU 44 of the patient handling device 22.

A processing station 50 is in communication with the network 32 to process data and/or information received from the various systems 24, 26, 28, 30, 42 or the patient handling device 22 via the communication module 48 to configure or control the various systems 24, 26, 28, 30, 42 or the patient handling device 22. In one embodiment, the processing station 50 is positioned at a central nurse's station in the healthcare facility and is implemented in a workstation, e.g., a personal computer, for use at the central nurse station. The workstation may include software configured to manipulate data and/or information received from the various systems 24, 26, 28, 30, 42 or the patient handling device 22. For instance, the workstation may be configured to receive data and/or information from the communication module 48 of the patient handling device 22 or to transfer data and/or information back to the patient handling device 22. Such data may originate from a bed exit detection system, a bed height detection system, a weight scale, a siderail sensing system that detects a position of the siderails, a therapy mattress, and the like. The processing station 50 preferably includes a graphical user interface on a touch-screen display for reviewing and manipulating the data and/or information. It should be appreciated that the processing station 50 may also be a stand-alone unit that is not located on the network 32, but includes the necessary hardware to link to the communication module 48 of the patient handling device 22.

Figure 2:
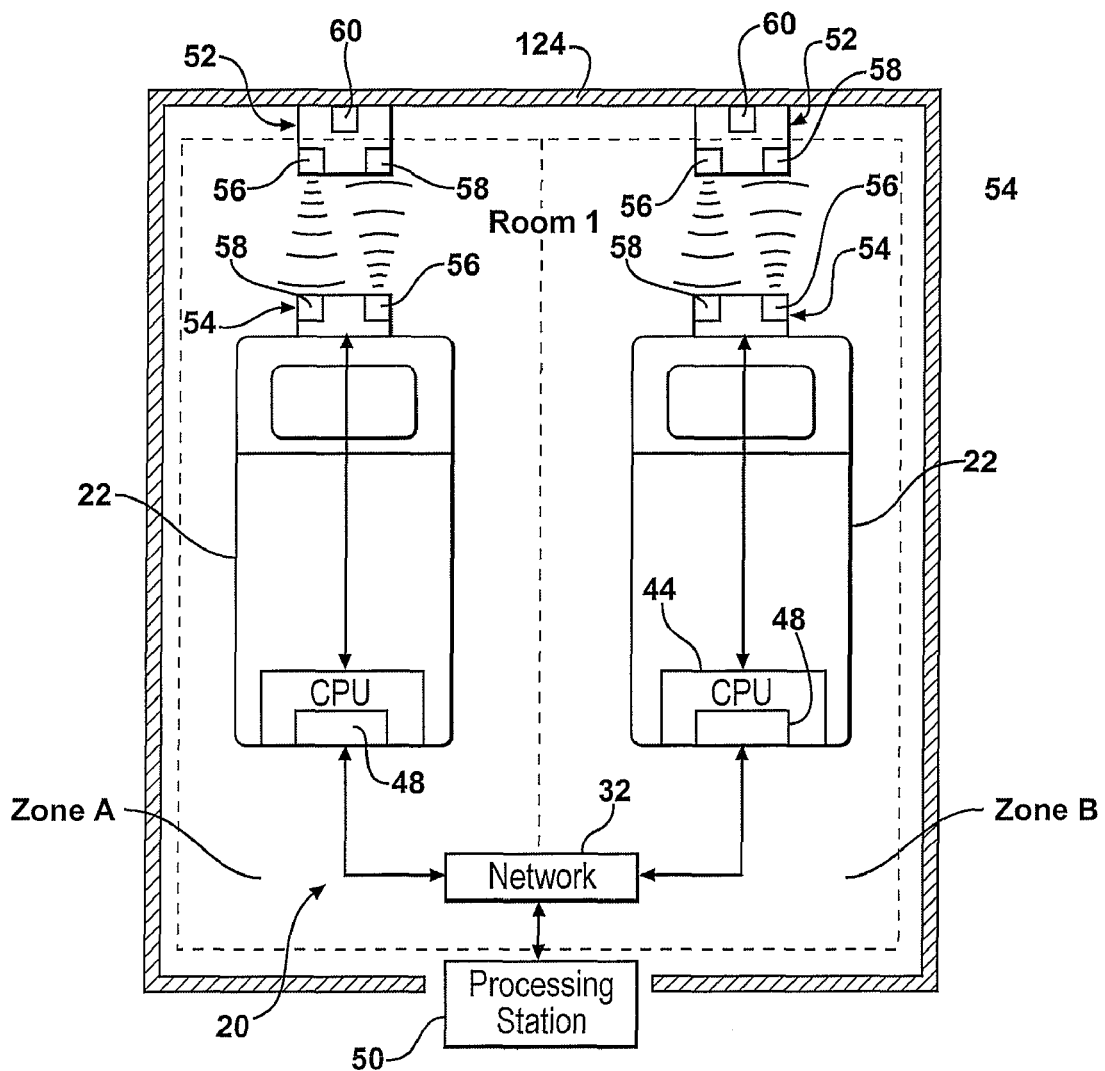
FIG. 2 is a top view of a typical room floor plan in the healthcare facility with two zones labeled A and B, schematically illustrating a location detection system of the present invention utilizing a locator configured for transmitting a unique location identifier to a receiver located on a patient handling device.

Referring to FIG. 2, a typical room floor plan in a healthcare facility is illustrated. As shown, the room, labeled Room 1, includes two zones, labeled Zone A and Zone B. These zones A, B are also often referred to as bed bays or bed areas. The location detection system 20 of the present invention is configured to determine the particular zone in which the patient handling device 22 is located. In the embodiment of FIG. 2, two patient handling devices 22 are illustrated for positioning at a location, e.g., Zone A and Zone B, in the healthcare facility. The location detection system 20 shall only be described with reference to one of the patient handling devices 22. Of course, it should be appreciated that the location detection system 20 is utilized to determine the specific locations of several patient handling devices 22 simultaneously throughout the health care facility. Multiple patient handling devices 22 may also be located in the same zone A, B.

Referring to the patient handling device 22 shown in Zone A of the room floor plan of FIG. 2, a locator 52 is fixed relative to the patient handling device 22. The locator 52 is affixed to a wall of the room, a floor of the room, or a ceiling of the room. The locator 52 may also be suspended from any location in the room such as by a tether or any other restraining mechanisms or devices adapted to maintain the locator 52 in a fixed relationship relative to the patient handling device 22. In other words, in the embodiment of FIG. 2, the locator 52 is not designed to be mobile for transport outside of the room. The locator 52 is programmed with a unique location identifier that corresponds to the location of the patient handling device 22. The unique location identifier may simply be a serial number of the locator 52 that is entered into a look-up table stored in accessible memory of the processing station 50 and associated with the zone in which the locator 52 is installed.

The processing station 50, which is remotely located relative to the patient handling device 22 and the locator 52, receives the unique location identifier such that the location of the patient handling device 22 can be determined and monitored remotely from the patient handling device 22. More specifically, a receiver 54 is supported by the patient handling device 22 and receives the unique location identifier corresponding to the location, and the communication module 48, which is electronically coupled to the receiver 54, transmits the unique location identifier of the locator 52 from the patient handling device 22 to the processing station 50. As a result, the patient handling device 22 acts as a communication link between the locator 52 and the processing station 50. About the same time, the communication module 48 transmits or communicates a unique ID of the patient handling device 22 to the processing station 50 such that the processing station 50 can correlate the location of the patient handling device 22 with the unique ID of the patient handling device 22.

A separate look-up table is utilized by the processing station 50 to correlate the unique ID to a patient for which the specific patient handling device 22 is associated. The processing station 50 then correlates the unique ID and patient to the particular zone in which the specific patient handling device 22 is now located such that the software application installed on the processing station 50 can accurately manage data corresponding to the specific patient handling device 22 and the patient.

In one embodiment, the locator 52 includes at least one infrared transmitter 56 for transmitting the unique location identifier to the receiver 54 and the receiver 54 includes a housing supporting at least one infrared sensor 58 for receiving the unique location identifier from the infrared transmitter 56. In this instance, transmitting the unique location identifier from the locator 52 to the patient handling device 22 is further defined as transmitting an infrared location signal from the at least one infrared transmitter 56 of the locator 52 to the at least one infrared sensor 58 of the receiver 54. Those skilled in the art appreciate that other data, besides the unique location identification may also be transmitted from the infrared transmitter 56, e.g., battery strength of a battery 60 in the locator 52, time/date, etc.

The receiver 54 is configured to include at least one infrared transmitter 56 for transmitting a request signal to the locator 52. Likewise, the locator 52 is configured to include at least one infrared sensor 58 to receive the request signal from the receiver 54. The battery 60, rechargeable or otherwise, is used to power the locator 52. To conserve battery life, the locator 52 normally operates in a sleep mode until the request signal is received by the at least one infrared sensor 58 of the locator 52.

Figure 3:
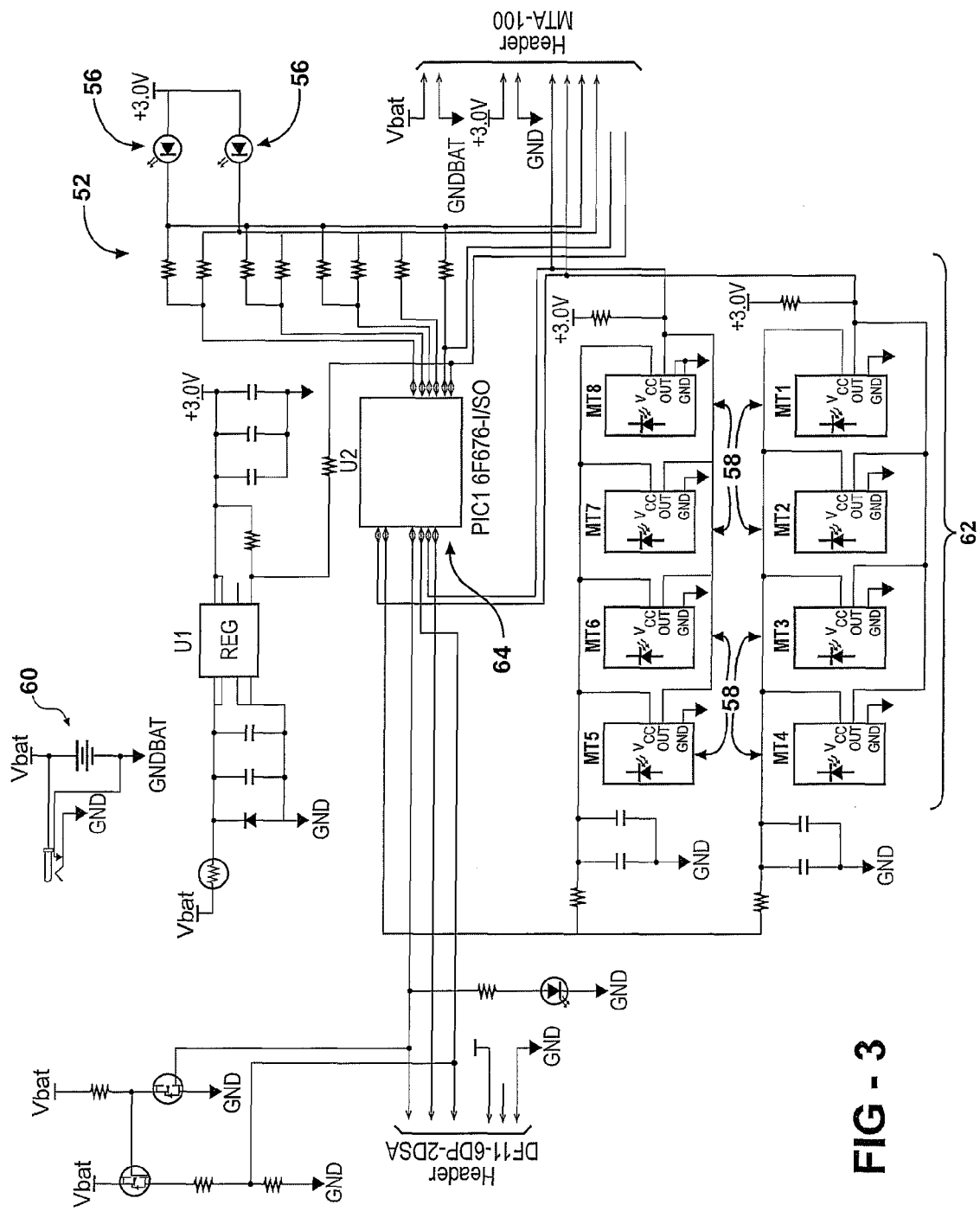
FIG. 3 is an electrical schematic of the locator of FIG. 2.

Referring to the electrical schematic of FIG. 3, one embodiment of the locator 52 is shown in more detail. In this embodiment, the locator 52 includes a plurality of infrared transmitters 56 for transmitting the unique location identifier to the receiver 54. Likewise, the locator 52 includes a plurality of infrared sensors 58 arranged in a sensor array 62 for receiving the request signal from the receiver 54. The locator 52 also includes a microprocessor 64 electrically coupled to the sensor array 62 and the infrared transmitters 56. The microprocessor 64 is pre-programmed with the unique location identifier that corresponds to the location of the patient handling device 22 and controls the infrared transmitters 56 to produce a signal with the unique location identifier and transmit the signal to the receiver 54 of the patient handling device 22. The infrared transmitters 56 of the locator 52 are adapted to provide variable power transmission to minimize cross talk and maximize signal integrity. The locator 52 is also adapted to modulate light intensity from the infrared transmitters 56 to maximize noise immunity. Finally, a filter (not shown) may be used to filter the infrared signal to reduce receiver saturation and maximize signal integrity and noise immunity.

Figure 4:
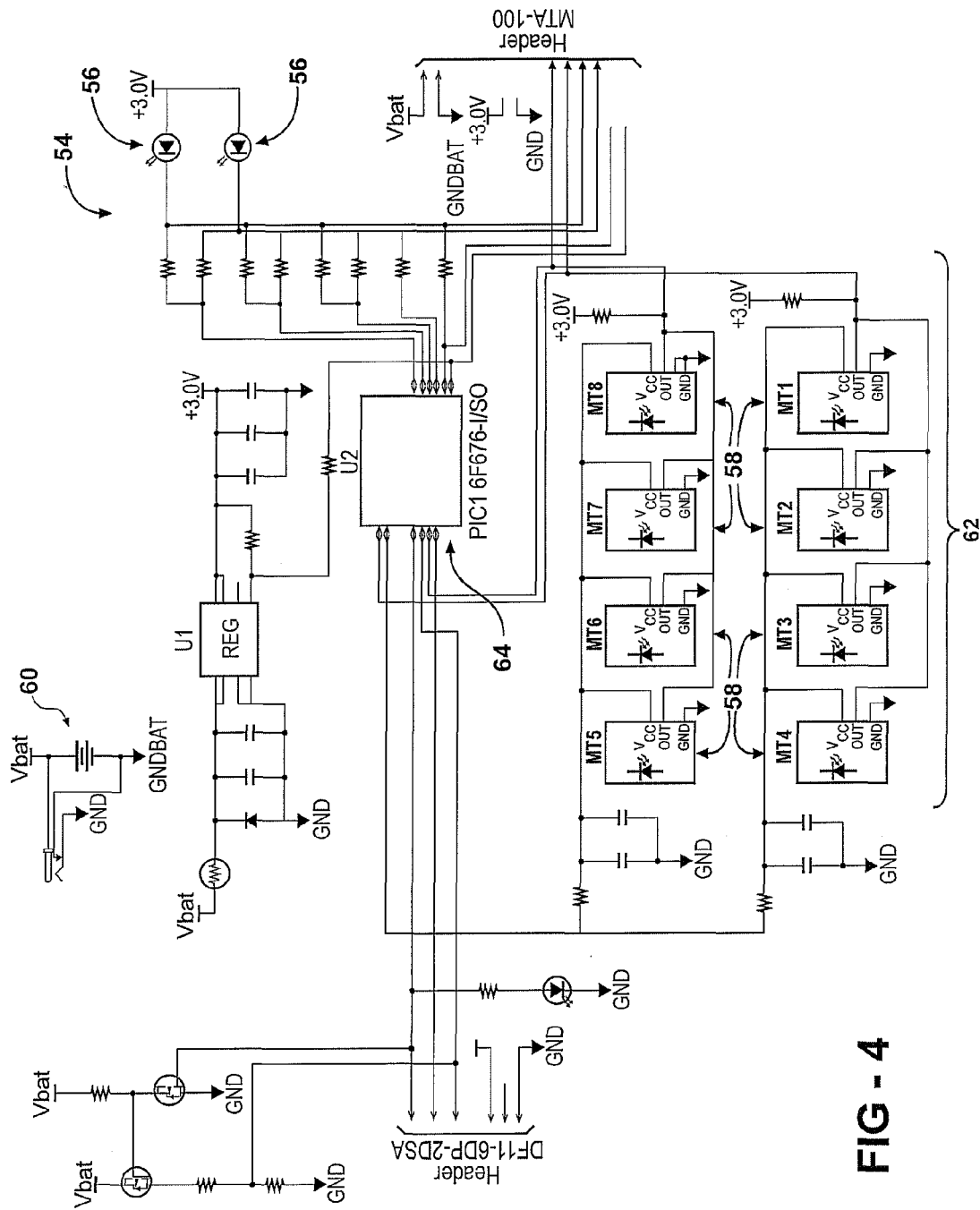
FIG. 4 is an electrical schematic of the receiver of FIG. 2.

Referring to the electrical schematic of FIG. 4, one embodiment of the receiver 54 of the patient handling device 22 is shown in more detail. In this embodiment, the receiver 54 includes a plurality of infrared sensors 58 arranged in a sensor array 62 for receiving the unique location identifier from the infrared transmitters 56 thereby improving transmission of the unique location identifier. Likewise, the receiver 54 includes a plurality of infrared transmitters 56 for transmitting the request signal from the receiver 54 to the locator 52 thereby improving transmission of the request signal. The receiver 54 may also be battery powered, but is preferably powered by an AC power source used to power a control system and the CPU 44 of the patient handling device 22. Those skilled in the art realize that the locator 52 and receiver 54 may each be implemented with a single infrared transmitter 56 and infrared sensor 58.

Figure 5:
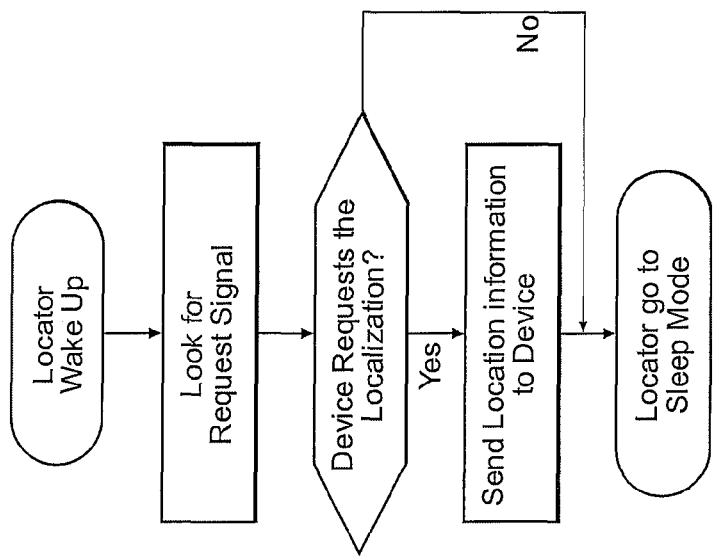
FIG. 5 is a process flow diagram illustrating a process for transmitting the unique location identifier from the locator to the receiver.

Referring to FIG. 5, a process flow diagram illustrates a method of detecting the location of the patient handling device 22. Initially, the locator 52 is in the sleep mode and awaits the request signal from the receiver 54. In other words, the microprocessor 64 looks on a reception channel to see if the patient handling device 22 has requested location information, e.g., the unique location identifier. If the patient handling device 22 has not requested the unique location identifier, the locator 52 remains in the sleep mode. If the patient handling device 22 sends the request signal and the request signal is properly received and understood by the locator 52, then the location signal sends the location information, i.e., the unique location identifier on a transmission channel. Once the unique location identifier is sent, the locator 52 returns to the sleep mode to conserve battery life.

Figure 6:
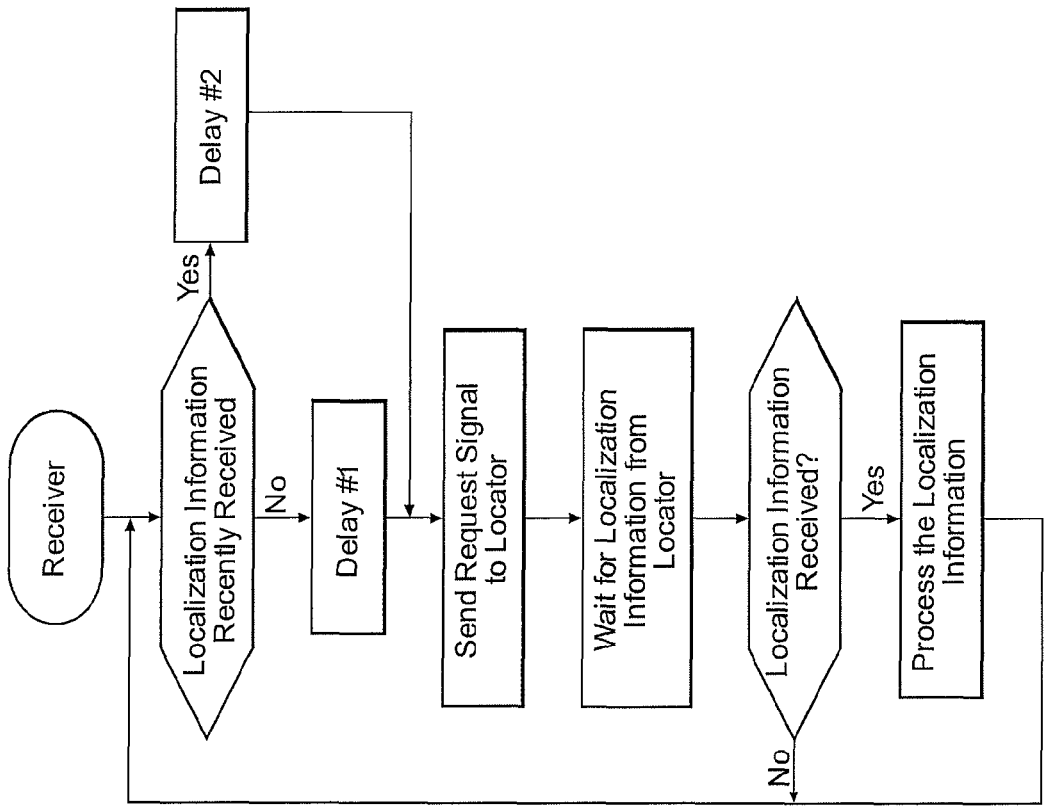
FIG. 6 is a process flow diagram illustrating a process for requesting the unique location identifier from the locator.

Referring to FIG. 6, a process flow diagram illustrates a method of sending the request signal to the locator 52 from the receiver 54. The receiver 54, which is preferably powered by an AC power source, regularly transmits the request signal to continually update the location of the patient handling device 22. The timing of these transmissions can differ depending on whether or not the receiver 54 has recently received the location information or not. As a result, there may be multiple predetermined delays between request signals, e.g., delay #1 and delay #2, which differ in the amount of time between transmissions of the request signal to the locator 52 on a transmission channel of the receiver 54. Once the location information is received, the information is processed and the unique location identifier is sent on to the CPU 44 and ultimately the processing station 50 to determine the location of the patient handling device 22.

Figure 7:
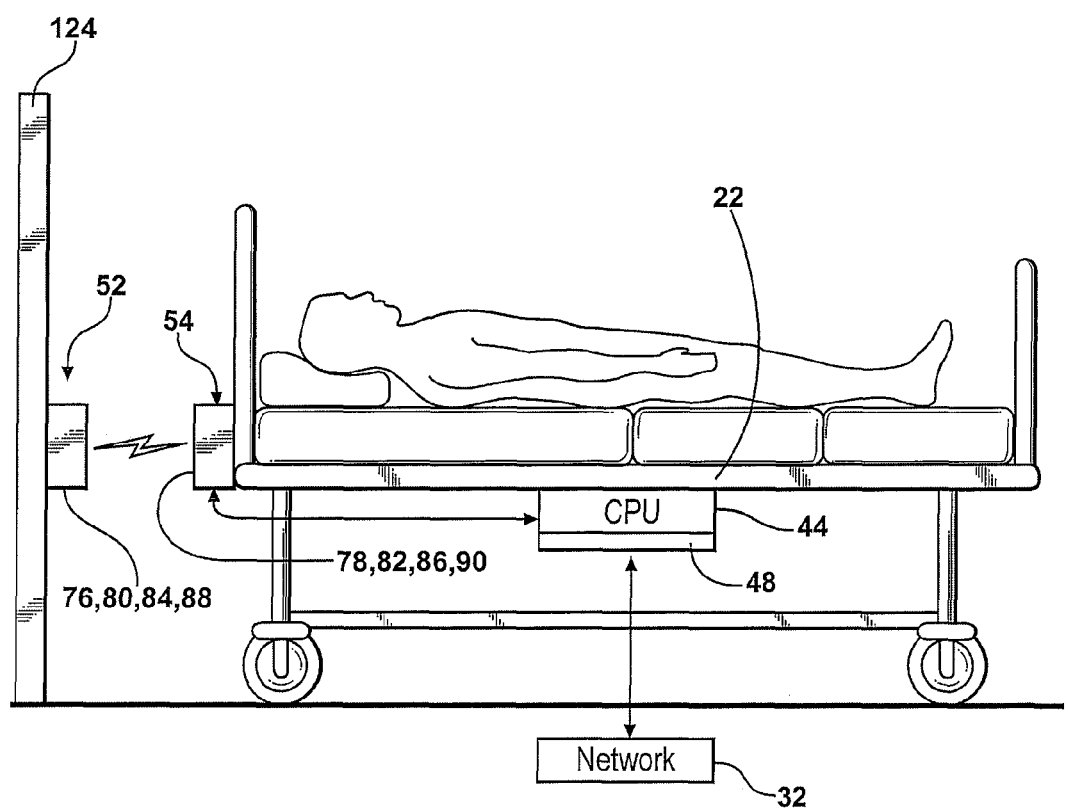
FIG. 7 is a perspective view illustrating alternative location detection systems of the present invention utilizing radio frequency, magnetic inductance, ultrasonic, or modulated light systems.

Referring to FIG. 7, alternative location detection systems are shown with similar features to that of the previously described embodiment. In FIG. 7, the locator 52 may be one of: a radio frequency identification (RFID) tag 76 for transmitting the unique location identifier using radio frequency; an ultrasonic transmitter 80 for transmitting the unique location identifier using ultrasonic signals; an inductively coupled transmitter 84 for transmitting the unique location identifier using principles of magnetic inductive coupling; or a modulated light transmitter 88 for transmitting the unique location identifier using modulated light. It should be appreciated that in each of these embodiments, the receiver 54 is particularly adapted for receiving the specific signal types mentioned, i.e., the receiver 54 may be a RFID reader 78, or include an ultrasonic sensor 82, an inductively coupled sensor 86, or a modulated light sensor 90.

Referring to FIGS. 8-11, further alternative systems using RFID are shown. It should be appreciated that any of the systems using RFID could be active, semi-active, or passive RFID systems as is well known to those skilled in the art. In general, when a passive system is employed, each of the tags 76 described contains a transponder (not shown) with a digital memory chip (not shown) that is given or programmed with the unique location identifier. An interrogator (not shown), which is an antenna packaged with a transceiver and decoder in the RFID reader 78 emits a signal activating the RFID tags 76 so that the interrogator can read and write data to the RFID tags 76. When the patient handling device 22 is moved into the particular zone in the room, the RFID tags 76 detect the RFID reader's activation signal. The RFID reader 78 then decodes the data, e.g., the unique location identifier, encoded in the RFID tag's digital memory chip and the data is passed to the processing station 50 as previously described.

Figure 8:
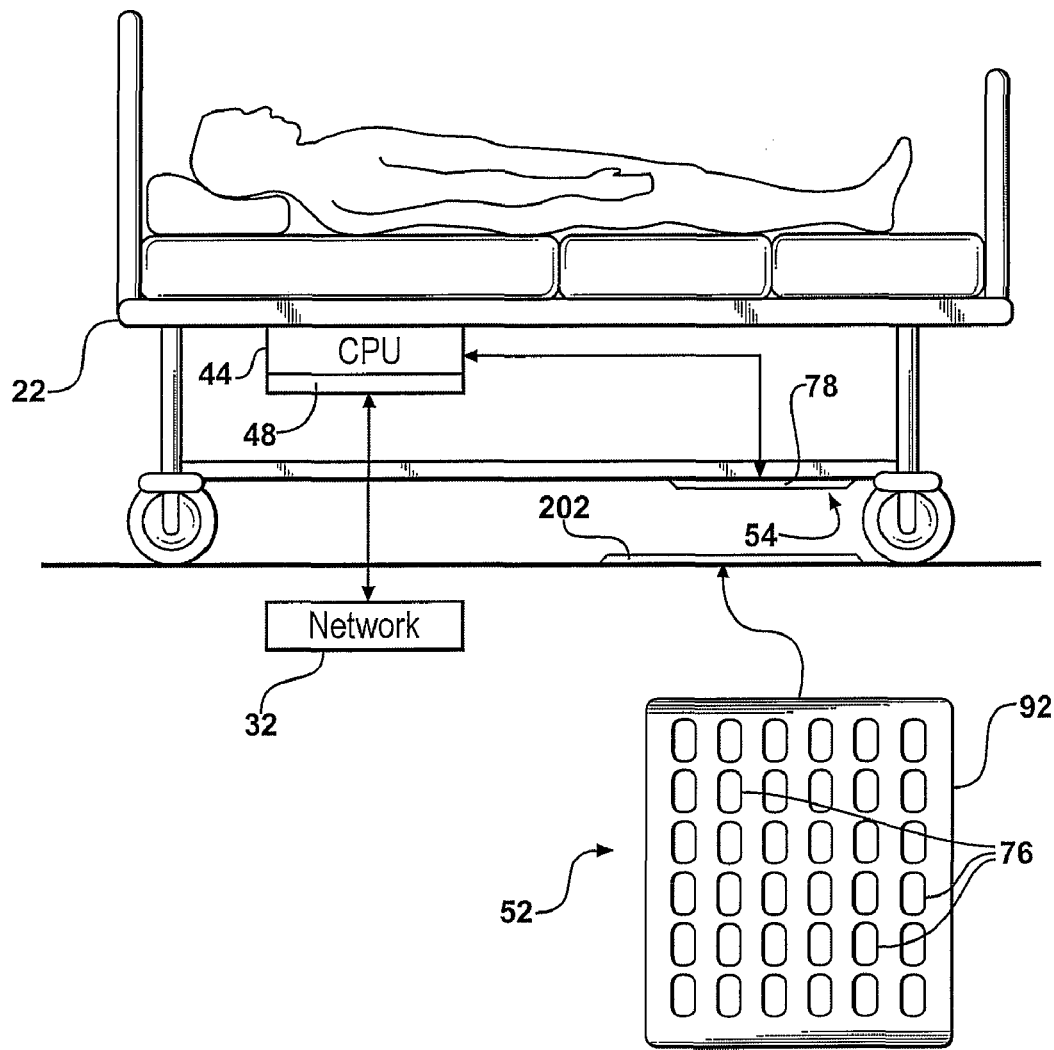
FIG. 8 is a perspective view illustrating an alternative location detection system of the present invention utilizing an array of RFID tags.

In the embodiment of FIG. 8, the locator 52 comprises an RFID tag mat 92 that includes an array of RFID tags 76. At least one of the tags 76 transmits the unique location identifier, or a selected set of the RFID tags 76 transmits a signal that is recognized as the unique location identifier. In this embodiment, the receiver 54 is an RFID reader 78 for receiving the signals from the RFID tags 76. In use, the healthcare professional or other employee of the healthcare facility would first move the patient handling device 22 into position either over the RFID tag mat 92 or in close proximity to the RFID tag mat 92. The RFID tags 76, or at least a portion thereof, would then transmit the unique location identifier to the RFID reader 78, which would then transmit the unique location identifier to the CPU 44 and then to the processing station 50 located on the network 32 via the communication module 48, as previously described.

Figure 9:
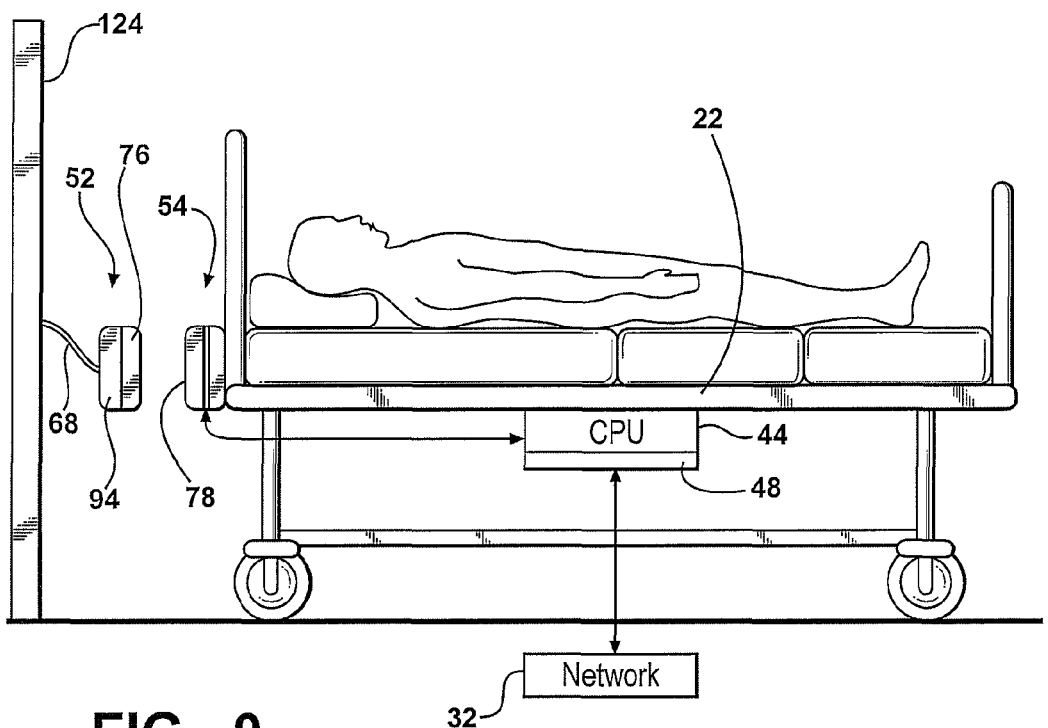
FIG. 9 is a perspective view illustrating an alternative location detection system of the present invention utilizing an RFID swipe card.

In the embodiment of FIG. 9, the locator 52 comprises an RFID swipe card 94 having at least one active or passive RFID tag 76. The RFID swipe card 94 is tethered to a head wall 124 of the room using a tether 68. This fixes the RFID swipe card 94 in the room relative to the patient handling device 22. The receiver 54 is an RFID reader 78 that receives the unique location identifier from the RFID tag 76 embedded in the RFID swipe card 94. In this embodiment, a healthcare professional would first move the patient handling device 22 into position in the particular zone in the room and then swipe the RFID swipe card 94 over the RFID reader 78 to transfer the unique location identifier from the RFID tag 76 to the RFID reader 78 and on to the processing station 50.

Figure 10:
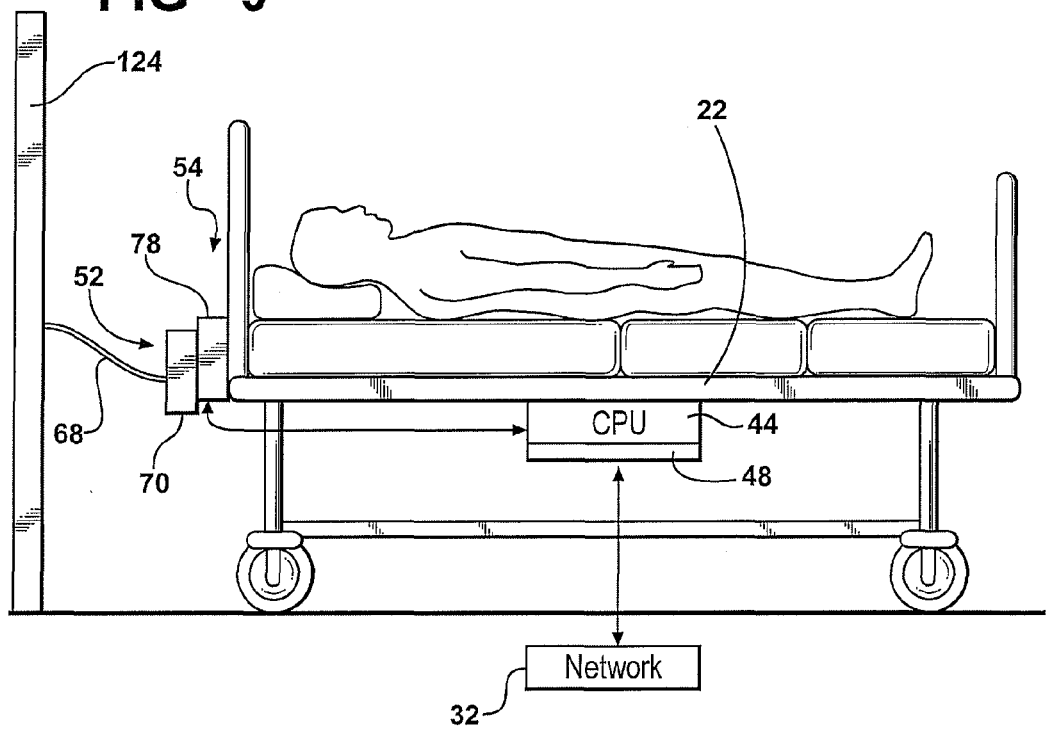
FIG. 10 is a perspective view illustrating an alternative location detection system of the present invention utilizing a tethered RFID magnet tag.

In the embodiment of FIG. 10, the locator 52 comprises a magnetic RFID tag 70. The magnetic RFID tag 70 is tethered to the head wall 124 as in FIG. 9, using a tether 68. However, in this embodiment, the healthcare professional or other employee of the healthcare facility does not merely swipe the magnetic RFID tag 70 to transmit the unique location identifier to the RFID reader 78. Instead, the RFID reader 78 magnetically attracts the magnetic RFID tag 70 to releasably lock the magnetic RFID tag 70 to the RFID reader 78 to ensure a complete transmission of the unique location identifier to the processing station 50 in the manner described above.

Figure 11:
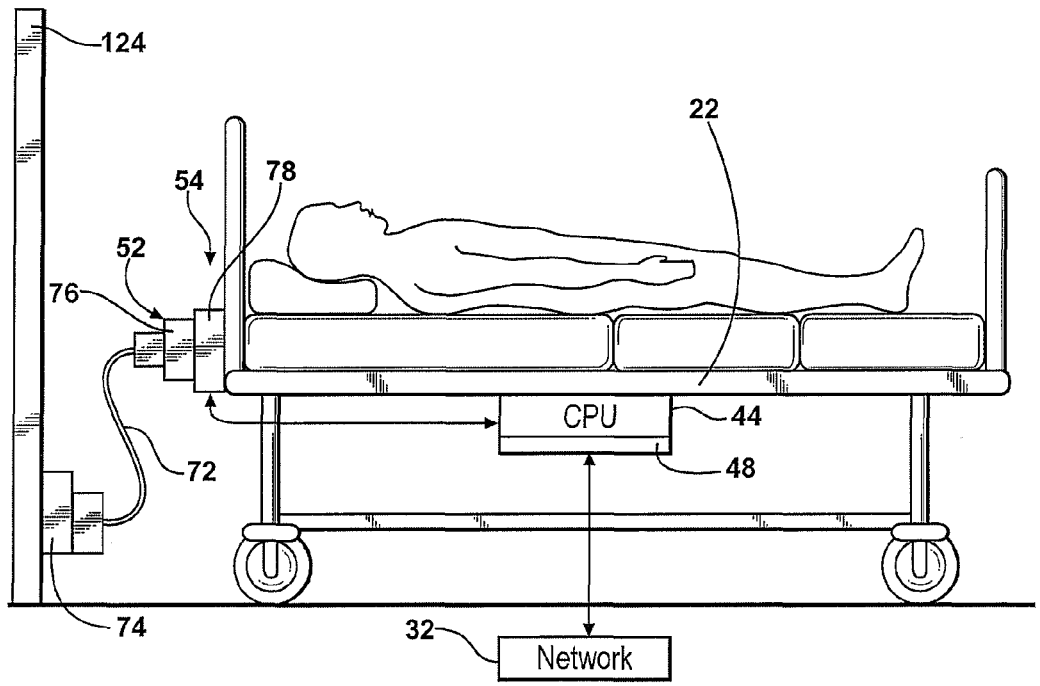
FIG. 11 is a perspective view illustrating an alternative location detection system of the present invention utilizing a nurse call cable with an integrated RFID tag.

In the embodiment of FIG. 11, the locator 52 comprises an RFID tag 76 and the receiver 54 comprises an RFID reader 78 similar to FIGS. 8-10. However, this embodiment further includes a cable 72 that would be maintained at each zone A, B. The cable 72 interconnects a nurse call interface of the patient handling device 22 to a standard nurse call interface port 74 located at each zone A, B. The RFID reader 78 is integrated into the nurse call interface located on the patient handling device 22 and the RFID tag 76 is integrated into an end of the cable 72 such that when the cable 72 connects the nurse call interface on the patient handling device to the nurse call interface port 74 mounted to the head wall 124, the RFID tag 76 would transmit the location information, e.g., unique location identifier, to the RFID reader 78 and on to the processing station 50 located on the network 32.

Figure 12:
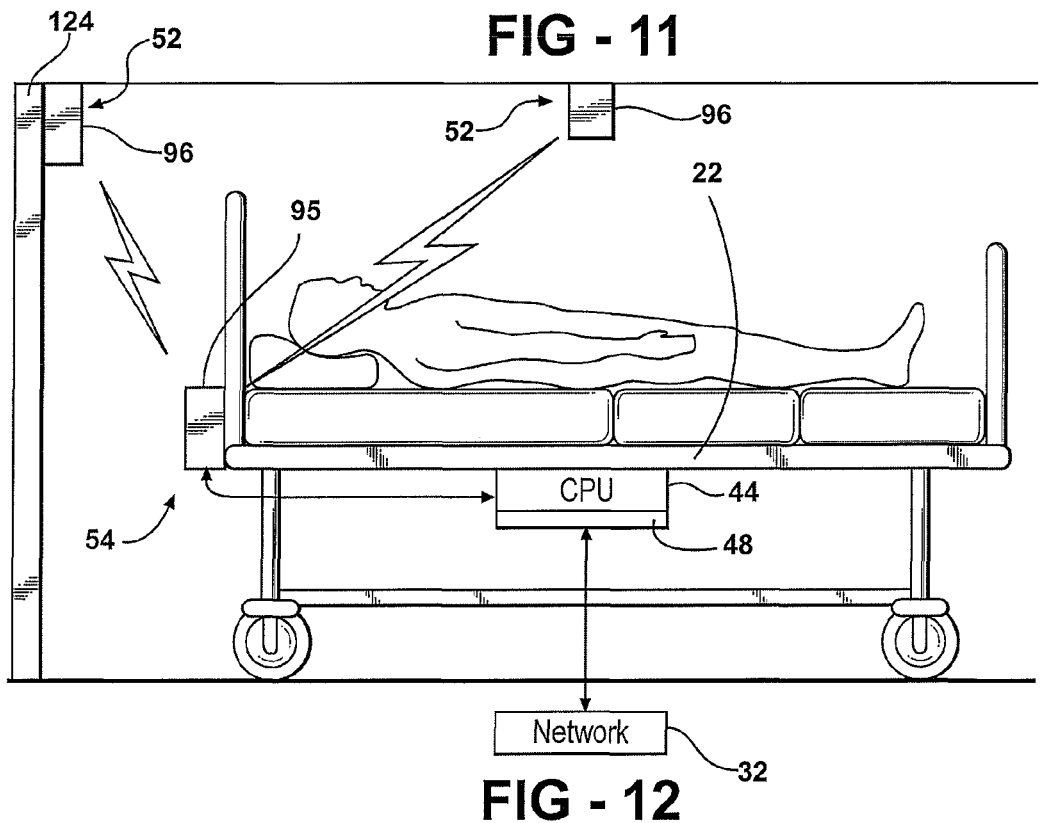
FIG. 12 is a perspective view illustrating an alternative location detection system of the present invention utilizing WiFi access points.

Referring to FIGS. 12-15, further alternative systems are shown. In the embodiment of FIG. 12, the locator 52 comprises a plurality of WiFi access points 96 located throughout the room and programmed with unique location identifiers for the zones in the room in which they are located. This system is capable of triangulating the room and zone location of the patient handling device 22 using the WiFi access points 96. The receiver 54 further comprises a WiFi transceiver 95 mounted to the patient handling device 22. The WiFi transceiver is in communication with the WiFi access points 96 to receive reference signals transmitted by the WiFi access points 96. In some embodiments, the strength of the signal received in combination with the unique location identifiers programmed into the WiFi access points 96 could be used to triangulate the room and zone location of the patient handling device 22. The WiFi transceiver 95 communicates the location information to the processing station 50 located on the network 32.

Figure 13:
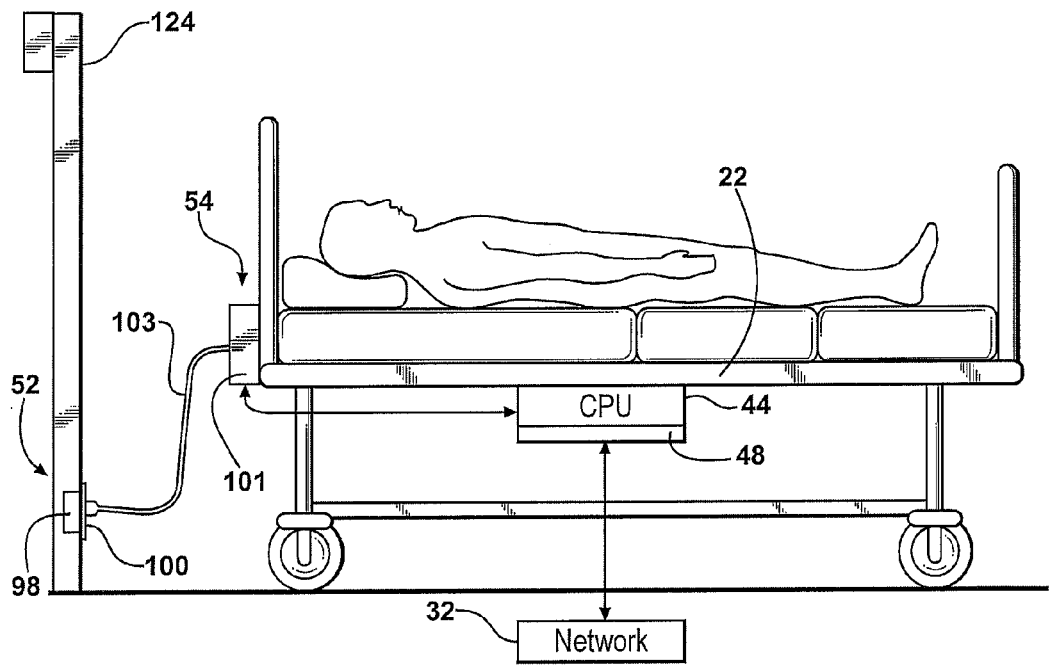
FIG. 13 is a perspective view illustrating an alternative location detection system of the present invention utilizing a power cord with and integrated ID transmitter.

In the embodiment of FIG. 13, the locator 52 comprises an ID transmitter 98 integrated into a 110 Volt AC plug 100 that transmits a reference signal to the receiver 54 located on the patient handling device 22. In this embodiment, the receiver 54 is integrated into a power cord interface 101 to communicate with the ID transmitter 98 through a power cord 103. The receiver 54 would then communicate the location information, e.g., unique location identifier, to the processing station 50 located on the network 32.

Figure 14:
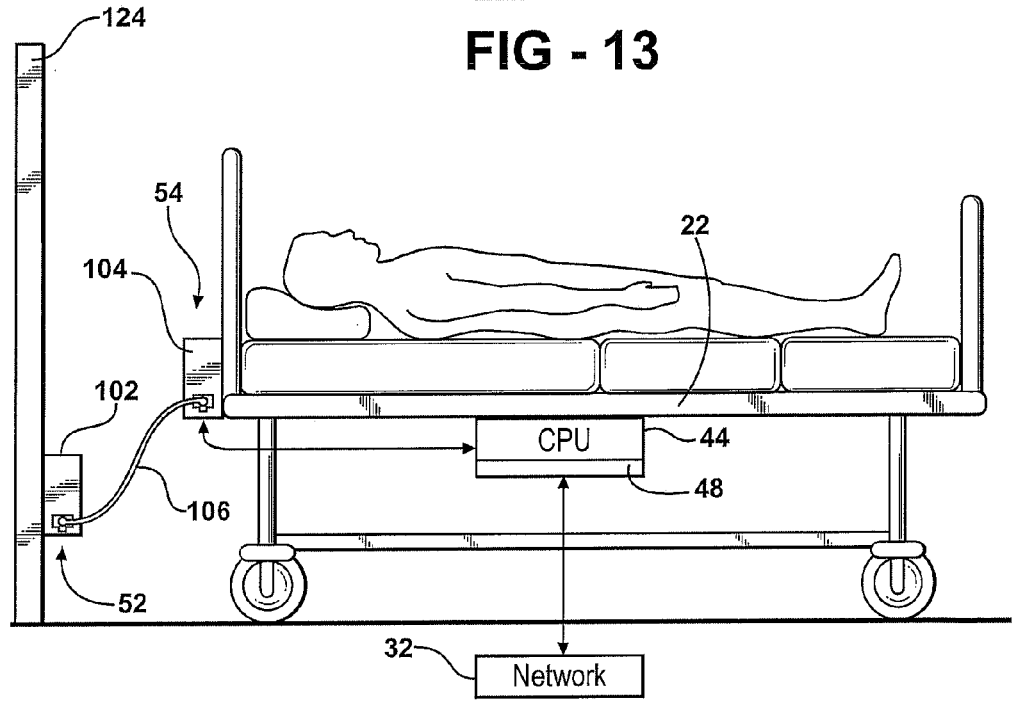
FIG. 14 is a perspective view illustrating an alternative location detection system of the present invention utilizing an Ethernet port to transmit the unique location identifier.

In the embodiment of FIG. 14, the locator 52 comprises an Ethernet port 102 and the receiver 54 comprises an Ethernet transceiver 104 mounted to the patient handling device 22. An Ethernet-compliant cable 106 interconnects the Ethernet transceiver 104 and the Ethernet Port 102 to send location information to the patient handling device 22. The Ethernet transceiver 104 then communicates the location information to the processing station 50.

Figure 15:
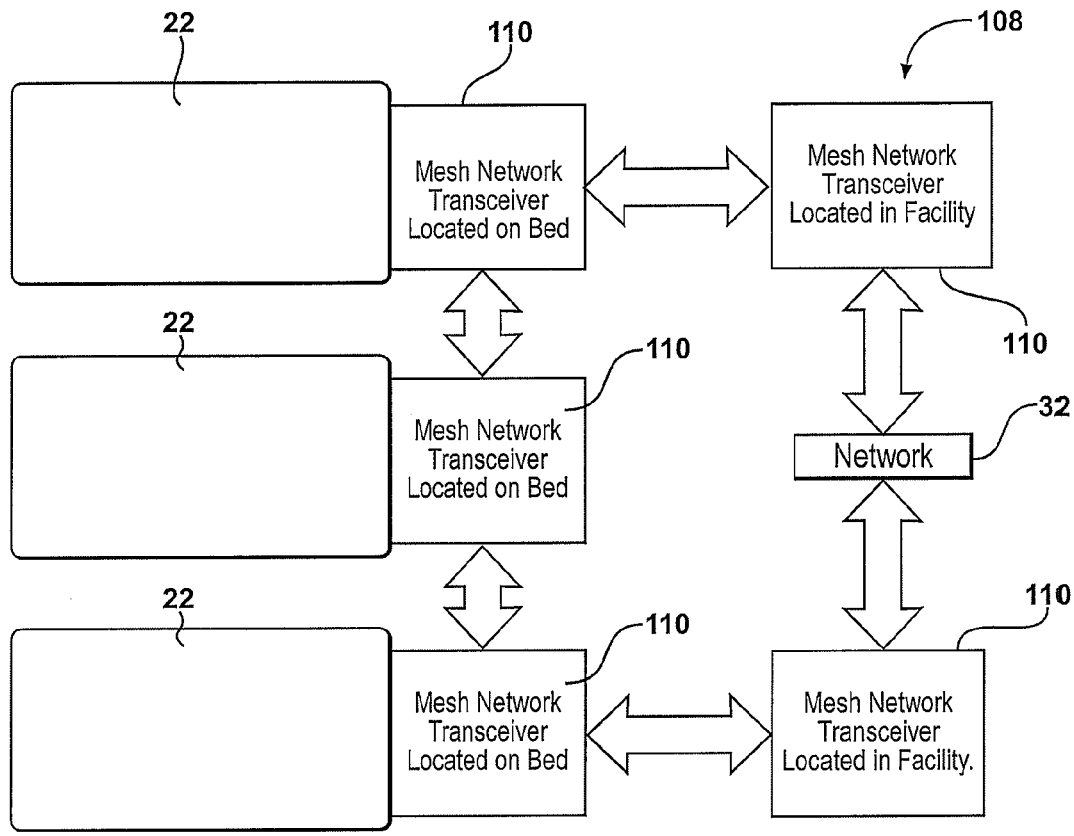
FIG. 15 is a schematic view illustrating an alternative location detection system of the present invention utilizing a mesh network to determine the location of the patient handling device.

In the embodiment of FIG. 15, the system utilizes a mesh network 108 with mesh network transceivers 110 to determine the location information. The mesh network 108 may be wired or wireless, preferably wireless to reduce infrastructure costs. The wireless mesh network 108 allows mesh network transceivers 110 to transmit data through one another onto the network 32 and the processing station 50. In other words, in the wireless mesh network 108, access points and wireless devices can organize themselves into an ad hoc network, communicating with each other to determine the fastest way to send data to the network 32. In the wireless mesh network 108, data hops from mesh network transceiver 110 to mesh network transceiver 110 looking for the shortest available path to the network 32 and the processing station 50. Here, each of the patient handling devices 22 is equipped with a mesh network transceiver 110, which acts as a node on the mesh network 108. The location information is obtained by knowing the association of the mesh network transceivers 110 on the patient handling devices 22 relative to the other mesh network transceivers 110 and/or a base transceiver (not shown). For instance, adjacent patient handling devices 22 in a second zone of the room, e.g., Zone B of Room 1, could determine the location information using the mesh network transceiver 110 on the patient handling device 22 in Zone A of Room 1.

Referring to FIGS. 16-19, alternative location detection systems are shown for determining the location in which the patient handling device 22 is located by separately determining first and second areas of the location. In one embodiment, the first area is the room, e.g., Room 1, in which the patient handling device 22 is located, and the second, subarea, is the zone in the room in which the patient handling device 22 is located, e.g., zones A, B. One of the previously described location detection systems may be used to determine the first area in which the patient handling device 22 is located. In this instance, the previously described systems would be enabled to only provide first area or room locations and not specific zone locations. In other words, the previously described systems would provide a first locating device, e.g., locator 52, mesh network transceiver 54, etc., associated with the patient handling device 22 and in communication with the processing station 50 to transmit a first unique location identifier to the processing station 50. The first unique location identifier being associated with the first area in which the patient handling device 22 is located, but not the subarea or particular zone in which the patient handling device 22 is located.

The asset tracking system 42 of the healthcare facility could also be the first locating device used for this purpose. In this instance, each of the patient handling devices 22 would be equipped with an asset tag 114 for tracking the patient handling devices 22 in the healthcare facility with the asset tracking system 42 being adapted to provide room locations for the patient handling devices 22 and transmit those room locations to an asset tag receiver 116 on the network 32, and on to the processing station 50. For purposes of description, reference is made to the first locating device being the asset tracking system 42.

Figure 16:
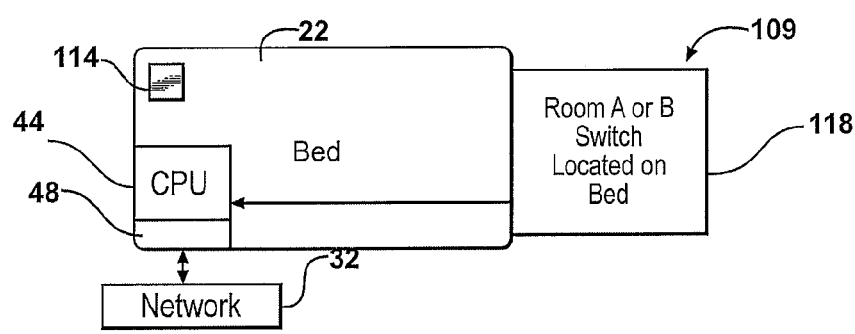
FIG. 16 is a schematic view illustrating an alternative location detection system of the present invention utilizing an asset tag in combination with a switch.

The alternative location detection systems of FIGS. 16-19 provide a second locating device 109 associated with the patient handling device 22 and in electronic communication with the processing station 50 to transmit a second unique location identifier to the processing station 50. The second unique location identifier corresponds to the subarea or zone in which the patient handling device 22 is located. Thus, the first unique location identifier provides the general vicinity in which the patient handling device 22 is located, while the second unique location identifier further refines the description of the location to pinpoint the location of the patient handling device 22. Referring first to FIG. 16, the second locating device may be an electronic switch 118 that can be manually actuated to correspond to the appropriate zone A, B.

The switch 118 would be in communication with the network 32 and processing station 50 to identify the zone A, B selected.

Figure 17:
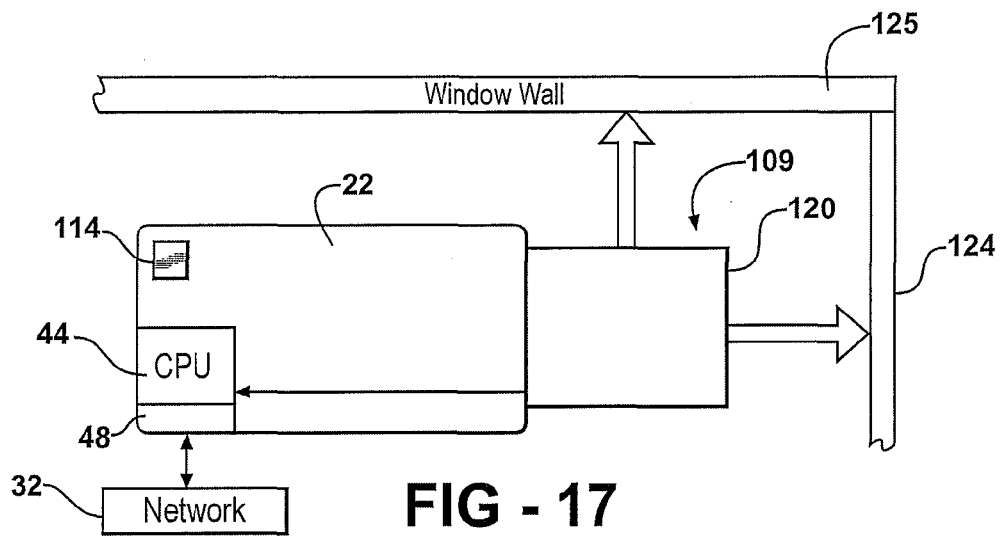
FIG. 17 is a schematic view illustrating an alternative location detection system of the present invention utilizing an asset tag in combination with a sonic distance finder.
Figure 18:
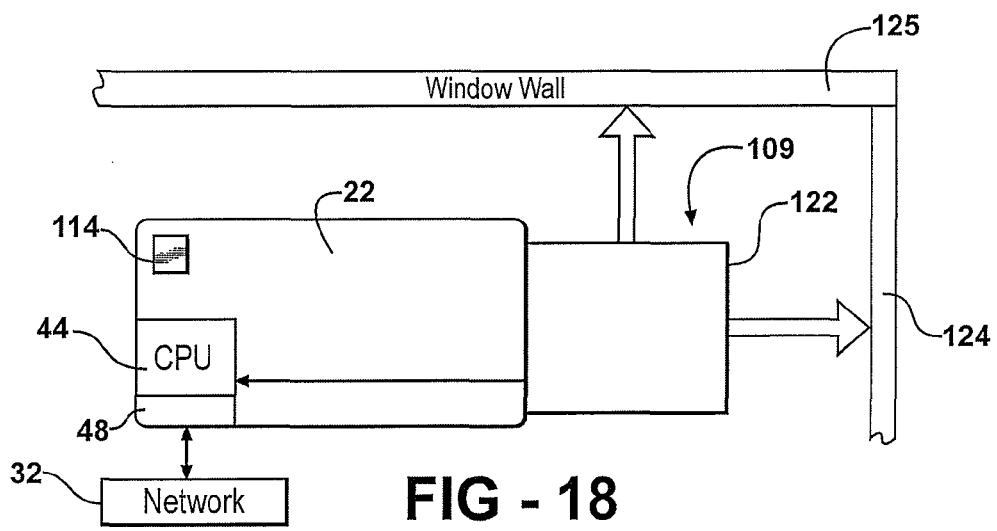
FIG. 18 is a schematic view illustrating an alternative location detection system of the present invention utilizing an asset tag in combination with a laser distance finder.

Referring to FIGS. 17 and 18, the second locating device 109 is a sonic distance sensor 120 or a laser distance finder 122 used to determine the zone A, B in which the patient handling device 22 is located. In these embodiments, the sonic distance sensors 120 or laser distance finders 122 would be adapted to generally measure distances from walls 124, 125 located in the first area, e.g., Room 1, to further determine the position of the patient handling device 22 in the room. A look-up table could be loaded into the processing station 50 with predetermined ranges of distances provided to correspond to the different zones A, B. For instance, once the patient handling device 22 is wheeled or moved into room, the sonic distance sensors 120 or laser distance finder 122 may be manually or automatically operated to measure the distance from predetermined boundaries, e.g., walls 124, 125, with the measured distances being compared to the look-up table and with a corresponding zone A, B selected therefrom.

Figure 19:
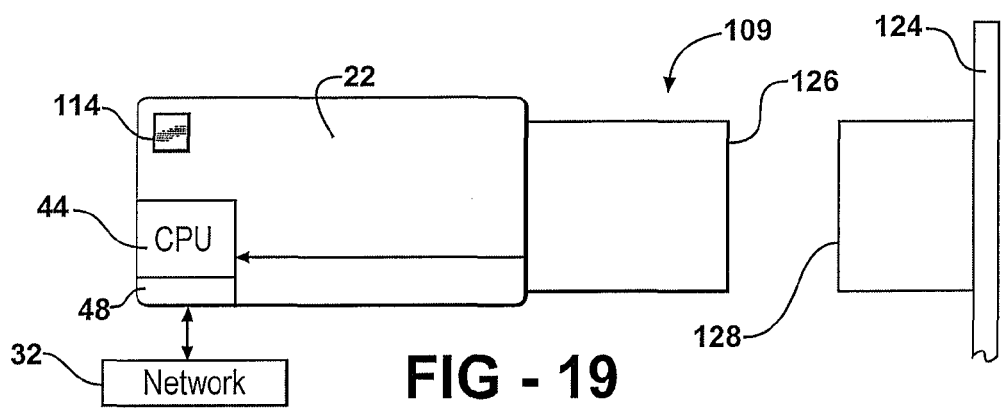
FIG. 19 is a schematic view illustrating an alternative location detection system of the present invention utilizing an asset tag in combination with a hall effect sensing system.

Referring to FIG. 19, the second locating device is a hall-effect sensor 126 operable with a room magnet 128 or plurality of room magnets 128 located in the room to determine the zone location of the patient handling device 22. In each of the embodiments of FIGS. 16-19, the sonic distance sensors 120, laser distance finder 122, and hall-effect sensor 126 would be adapted to transmit signals that communicate, either directly or indirectly, with the processing station 50 to display the room and zone location of the patient handling device 22. In one version, the communication module 48 is in electronic communication with these second locating devices 109 and the processing station 50 to transmit the second unique location identifier from the second locating devices 109 to the processing station 50. Again, as with the previously described embodiments, the patient handling device 22 has a unique ID and the communication module 48 communicates the unique ID to the processing station 50 such that the processing station 50 can correlate the first unique location identifier and the second unique location identifier to the patient handling device 22 to determine the room and zone location of the patient handling device 22.

Obviously, many modifications and variations of the present invention are possible in light of the above teachings. The invention may be practiced otherwise than as specifically described within the scope of the appended claims.

What is claimed is:

1. A location detection system for a facility, said location detection system comprising:
a patient handling device having a support surface for supporting a patient and being mobile for positioning at a location in the facility, said patient handling device further having circuitry for controlling one or more sensing, motor or therapy functions of said patient handling device and having a unique patient handling device ID, and said patient handling device including a network interface;
a location transmitting device spaced from the patient handling device for communicating a unique location identifier corresponding to the location of said patient handling device to said patient handling device;
wherein said circuitry is operable to send patient handling device status data, and said circuitry is operable to send said unique patient handling device ID and the unique location identifier from said patient handling device by way of said network interface.

2. A location detection system as set forth in claim 1, further comprising a remote computer that is operable to receive said unique patient handling device ID and the unique location identifier from said network interface and is operable to associate the patient handling device with the unique patient handling device ID and a location corresponding with the unique location identifier.

3. A location detection system as set forth in claim 2, wherein said remote computer comprises a nurse's station.

4. A location detection system as set forth in claim 2, wherein said remote computer is operable to receive said patient handling device status data.

5. A location detection system as set forth in claim 4, wherein said remote computer is operable for reviewing and manipulating said patient handling device status data.

6. A location detection system as set forth in claim 4, wherein said patient handling device comprises a bed, and said data originates from a bed exit detection system, a height detection system, a weight scale, a side rail sensing system that detects a position of the side rails, or a therapy mattress.

7. A location detection system as set forth in claim 1, wherein said circuitry comprises a plurality of electronic modules, said network interface comprising one of said modules.

8. A location detection system as set forth in claim 2, wherein said network interface is in communication with said remote computer via a communication link.

9. A location detection system as set forth in claim 8, wherein said communication link comprises a wireless communication link.

10. A location detection system as set forth in claim 8, wherein said remote computer includes a user interface for reviewing and manipulating said patient handling device status data.

11. A location detection system as set forth in claim 1, wherein said location transmitting device comprises a plurality of transmitting devices.

12. A location detection system as set forth in claim 11, wherein said plurality of transmitting devices comprise a plurality of wireless transmitting devices.

13. A method of detecting a location of a patient handling device having a support surface supporting the patient and being adapted to be transported throughout a facility, said method comprising:
  associating a unique patient handling device ID with a patient handling device;
  transmitting a unique location identifier corresponding to the location of the patient handling device from a location transmitting device spaced from the patient handling device;
  transmitting the unique location identifier and the unique patient handling device ID from the patient handling device to a remote computer device remote from the patient handling device;
  transmitting patient handling data to the remote computer device; and
  correlating the unique location identifier with the unique ID.

14. A method according to claim 13, wherein said transmitting the unique location identifier and the unique patient handling device ID comprises transmitting the unique location identifier and the unique patient handling device ID from the patient handling device via a network interface to a remote computer that is operable to receive said unique patient handling device ID and the unique location identifier from said network interface and is operable to associate the patient handling device with the unique patient handling device ID and a location corresponding with the unique location identifier.

15. A method according to claim 14, wherein said transmitting the unique location identifier and the unique patient handling device ID comprises transmitting the unique location identifier and the unique patient handling device ID to a nurse's station.

16. A method according to claim 14, further comprising viewing said patient handling data at said remote computer.

17. A method according to claim 16, further comprising manipulating said patient handling data at said remote computer.

18. A method according to claim 17, further comprising using a user interface at said remote computer to manipulate said patient handling data at said remote computer.

19. A method according to claim 14, wherein said transmitting patient handling data includes transmitting data from a bed exit detection system, a height detection system, a weight scale, a side rail sensing system that detects position of the side rails, or a therapy mattress.

20. A method according to claim 14, wherein said transmitting the unique location identifier and the unique patient handling device ID comprises transmitting the unique location identifier and the unique patient handling device ID wirelessly.

* * * * *